United States Patent
Spreitzer et al.

(10) Patent No.: US 6,861,567 B2
(45) Date of Patent: Mar. 1, 2005

(54) SPIRO COMPOUNDS, AND THEIR USE

(75) Inventors: Hubert Spreitzer, Viernheim (DE); Josef Salbeck, Kaufungen (DE); Frank Weissörtel, Donau (DE)

(73) Assignee: Covion Organic Semiconductors GmbH (DE)

( * ) Notice: Subject to any disclaimer, the term of this patent is extended or adjusted under 35 U.S.C. 154(b) by 0 days.

(21) Appl. No.: 10/243,302

(22) Filed: Sep. 13, 2002

(65) Prior Publication Data

US 2003/0065190 A1 Apr. 3, 2003

Related U.S. Application Data

(63) Continuation of application No. 09/601,435, filed as application No. PCT/EP99/00615 on Jan. 30, 1999, now abandoned.

(30) Foreign Application Priority Data

Feb. 4, 1998 (DE) .......................................... 198 04 310

(51) Int. Cl.$^7$ ...................... C07C 13/465; B32B 19/00
(52) U.S. Cl. ...................................... 585/27; 428/690
(58) Field of Search ............................ 585/27; 428/690

(56) References Cited

U.S. PATENT DOCUMENTS

| 3,781,711 A | | 12/1973 | Drexhage et al. | |
|---|---|---|---|---|
| 5,037,578 A | | 8/1991 | Kauffman et al. | |
| 5,041,238 A | | 8/1991 | Kauffman et al. | |
| 5,149,807 A | | 9/1992 | Hammond et al. | |
| 5,621,131 A | * | 4/1997 | Kreuder et al. | 558/46 |
| 5,840,217 A | * | 11/1998 | Lupo et al. | 252/583 |
| 5,885,368 A | | 3/1999 | Lupo et al. | |

FOREIGN PATENT DOCUMENTS

| DE | 3703065 A1 | 8/1987 |
|---|---|---|
| EP | 0 676 461 A2 | 10/1995 |
| WO | WO 97/10617 | 3/1997 |

OTHER PUBLICATIONS

CA:124:18003 abs of EP676461 Oct. 1995.*
CA:130:344493 abs of Proceedings of SPIE—The International Society for Optical Engineering—pp 40–48 3476 by Weinfurtner et al 1998.*
CA:126:163723 abs of Inorganic and Organic Electroluminescence by Salbeck J. pp 243–6 1996.*
CA:126:322720 abs of Polymer Preprints (Amer. Chem. Soc., Division of Polymer Chem.) 38 (1) pp 349–50 by Salbeck et al 1997.*
CA:129:5625 abs of WO 9818966 May 1998.*
CA 137:208193 abs of US 2002122900 Sep. 2002.*
CA:136:223477 abs of Chemistry of Materials by Geng et al 14(1) pp 463–470 14 (1) 2002.*
CA:138:330028 abs of JP2033115624 Apr. 2003.*
CA:136:309744 abs of Chemistry of Materials by Katsis et al 14(3) pp 1332–1339 2002.*
CA:128:41356 abs of Macromolecular Symposia by Salbeck et al pp 121–132 no 125 19980.*
CA:92:146733 abs of Helvetica Chimica Acta 62(7) pp 2285–302 by Prelog et al 1979.*
CA:89:131042 abs of Society of Dyers and Colourists 94 (7) pp 306–9 by Sutcliffe et al 1978.*
Sutcliffe, F.K. et al. *The Synthesis and Properties of Dyes and Pigments Containing A 9,9′–Spirobifluorene Residue.* Journal of the Society of Dyers and Colourists, vol. 94, No. 7, Jul. 1978, pp. 306–309, XP002030898.
Liphardt, B. et al. *Bifluorophore Laserfarbstoffe zur Steigerung des Wirkungsgrades von Farbstoff–Lasern Laser Dyes, I. Bifluorophoric Laser Dyes for Increase of the Efficiency of Dye Lasers.* Liebigs Annalen der Chemie, vol. 1981, No. 6, Jun. 1981, pp. 1118–1138, XP002030899 (with English abstract).
CA:113:41352 abs of J Am Chem Soc by Tour et al 112(14) pp 5662–3, 1990.
CA:126:311052 abs of DE 19533850, Sep. 1995.
CA:126:163723 abs of Inorg Org Electroluminescence (Int. Workshop Electroluminescence) 8$^{th}$ pp 243–246, 1996.
CA:130:344493 abs of Proc SPIE Int Soc Opt Eng (Organic Light–Emitting Materials and Devices II) 3476, 1998.
J. Salbeck et al., "Optical amplification in spiro–type molecular glasses", *Thin Solid Films*, vol. 417(1–2), pp. 20–25 (2002).

* cited by examiner

*Primary Examiner*—J. Parsa
(74) *Attorney, Agent, or Firm*—Connolly Bove Lodge & Hutz LLP

(57) ABSTRACT

The present invention relates to novel spiro compounds of the formula (I):

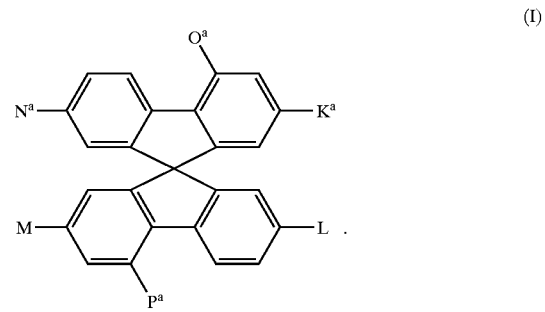

12 Claims, No Drawings

SPIRO COMPOUNDS, AND THEIR USE

RELATED APPLICATION

This application is a continuation of Ser. No. 09/601,435 filed Oct. 23, 2000, now abandoned which is a 371 national phase of PCT/EP99/00615, filed Jan. 30, 1999 which claims priority to German Application 19804310.4 filed Feb. 4, 1998.

Spiro compounds of the general formula:

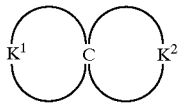

in which $K^1$ and $K^2$, independently of one another, are conjugated systems, have found application, for example, as electroluminescent materials (EP-A 0 676 461), as charge-transport layer in photovoltaic cells (WO-A 97/106 17), as materials in nonlinear optics (EP-A 0 768 563) and as optical brighteners (DE-A 196 45 063).

Surprisingly, it has now been found that certain spiro compounds which contain more than one spiro center are particularly suitable for use as laser dyes for organic solid lasers.

The invention therefore relates to spiro compounds of the formula (I):

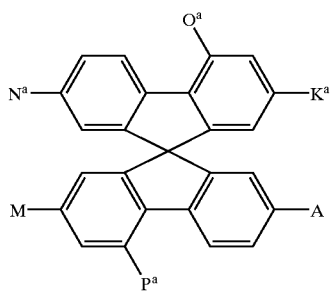

(I)

where $K^a$, L, M, $N^a$, $O^a$ and $P^a$, independently of one another, are identical or different and are

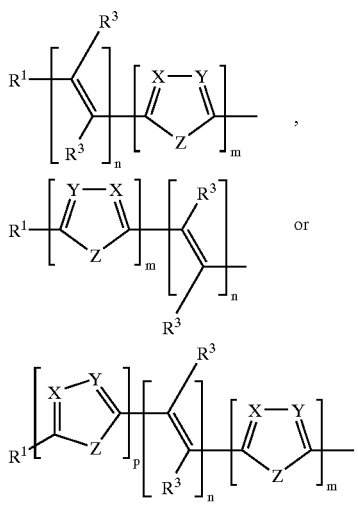

where the symbols and indices have the following meaning:
$R^3$ H, $C_1$–$C_{22}$-alkyl, CN, $C_6$–$C_{14}$-aryl, $C_4$–$C_{15}$-heteroaryl, $C_5$–$C_{20}$-alkylaryl or $C_5$–$C_{20}$-arylalkyl m, n, and p: independently of one another, identically or differently, 0, 1, 2, 3, 4, 5 or 6;
X and Y: CR or N
Z: O, S, NR, $CR_2$, —CH=CH—, —CH=N—, —$CR^2$=$CR^2$— or —$CR^2$=N—;
R: H, $C_1$–$C_{22}$-alkyl (linear, branched or cyclic), $C_1$–$C_{22}$-alkoxy, CN, $NR^2_2$, $COOR^2$, CHO, $SR^2$, $NO_2$, OH, $C_6$–$C_{14}$-aryl, such as phenyl, biphenyl, 1-naphthyl, 2-naphthyl or 9-anthryl, or $C_4$–$C_{15}$-heteroaryl, preferably containing one, two or three N, O and/or S atoms, particularly preferably 2-thienyl or 2-furanyl, or aryloxy,
$R^1$: independently of one another, identically or differently, R, A, B or C, where

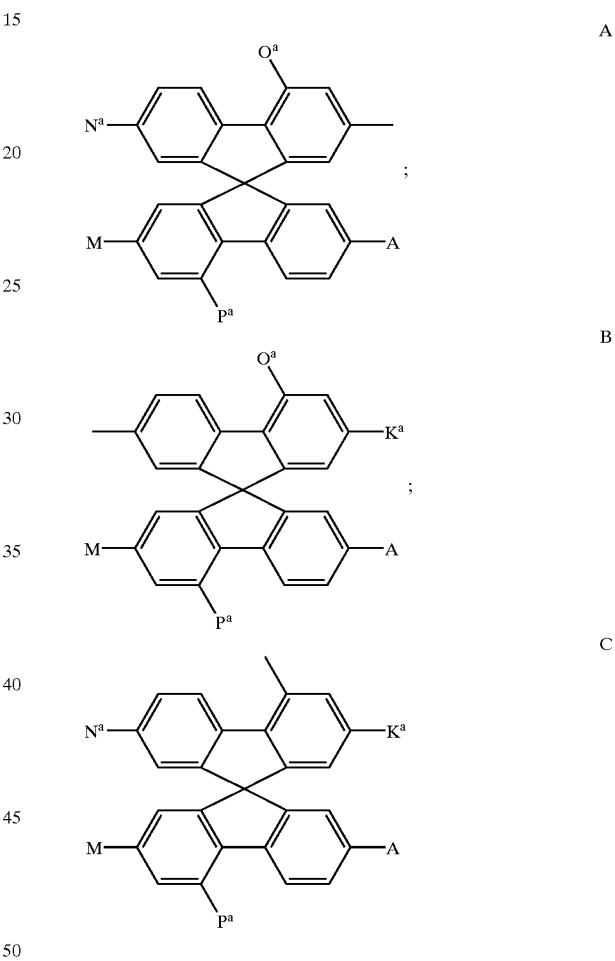

where at least one, preferably 1 to 10, radicals $R^1$ are selected from the radicals A, B or C;
$R^2$ is, identically or differently, H or a hydrocarbon radical having 1 to 30 carbon atoms, which may also contain one or more, preferably one, two or three, heteroatoms, preferably N, O and/or S,
with the exception of compounds of the formula (I) in which in $O^a$, $P^a$, M and L simultaneously $R^1$ is not A, B or C and at the same time in $K^a$ and $N^a$ $R^1$ is A or B
and compounds of the formula (I) in which in $O^a$, $K^a$, M and $P^a$ simultaneously $R^1$ is not A, B or C and at the same time in $N^a$ and L $R^1$ is A or B.

Preference is given to compounds of the formula (I) in which the symbols and indices have the following meanings:
n and p: 0;
m: 0, 1, 2, 3, 4, 5 or 6;
X and Y: CR;

Z: —CR=CR—; and

R¹: independently of one another, identically or differently, R, A, B or C, where at least one radical R¹ is A, B or C R³: H, $C_2$–$C_{10}$-alkyl or $C_6$–$C_{10}$-aryl In particularly preferred compounds of the formula (I), the radicals R¹ in $K^a$, L, M and $N^a$, independently of one another, are identically or differently A, B or C.

In very particularly preferred compounds of the formula (I), $O^a$ and $P^a$ are H.

In other very particularly preferred compounds of the formula (I), R¹, identically or differently, is A, B or C.

In other particularly preferred compounds of the formula (I), R¹ is R or A, where at least one R¹ is A.

In further very particularly preferred compounds of the formula (I), R¹ is A.

The number of groups A, B and/or C is preferably from 1 to 50, preferably from 1 to 20, particularly preferably from 1 to 10.

Compounds according to at least one of the preceding claims, wherein $O^a$ and $P^a$ in the formula (I) is H.

Particularly preferred compounds of the formula (I) are those of the formula (II):

$Q^1$ and $Q^2$: independently of one another, identically or differently, H or

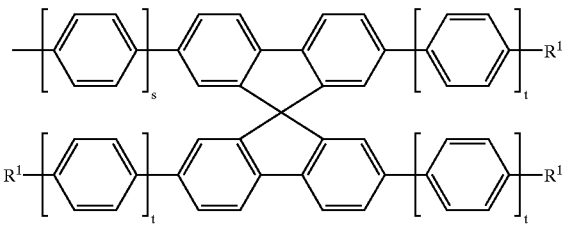

where s and t: independently of one another, identically or differently, are 0, 1, 2, 3 or 4; and R¹: independently of one another, identically or differently, is R or A, B or C, and at least one radical $Q^1$ or $Q^2$ is not hydrogen.

In preferred compounds of the formula (II), the symbols and indices have the following meanings:

$Q^1$ and $Q^2$: independently of one another, identically or differently, H or

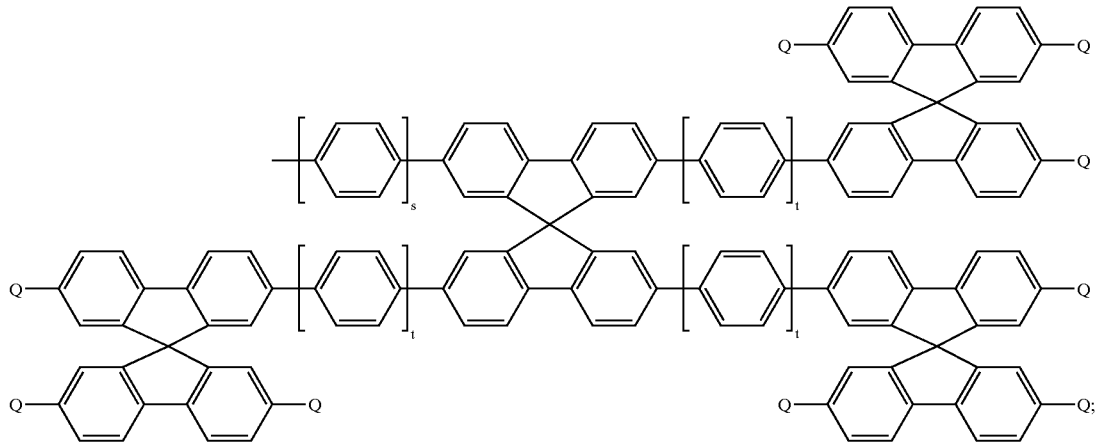

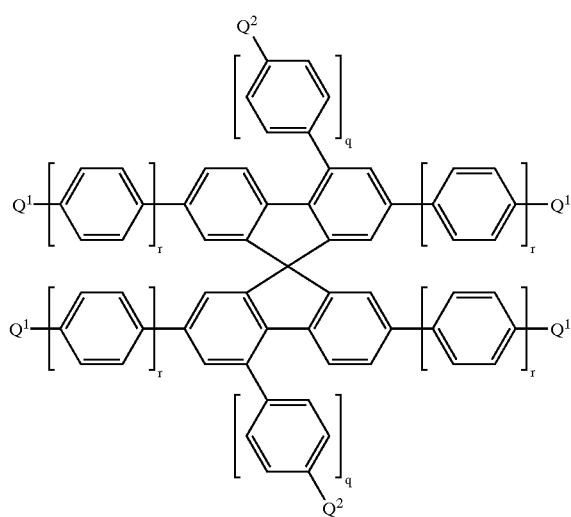

where the symbols and indices have the following meanings:

q and r: independently of one another, identically or differently, 0, 1, 2, 3, 4, 5 or 6;

where s and t: independently of one another, identically or differently, are 0, 1, 2, 3 or 4; and Q: independently of one another, identically or differently, is R or $Q^1$.

The spiro compounds according to the invention are prepared by methods known per se from the literature, as described in the standard works on organic synthesis, for example Houben-Weyl, Methoden der Organischen Chemie [Methods of Organic Chemistry], Georg-Thieme-Verlag, Stuttgart, and the corresponding volumes of the series "The Chemistry of Hetero-cyclic Compounds" by A. Weissberger and E. C. Taylor (editors).

The preparation is carried out under reaction conditions which are known and suitable for said reactions. Use can also be made here of variants which are known per se, but are not mentioned here in greater detail.

Compounds of the formula (II) in which $O^a$=$P^a$=H are obtained, for example, starting from 9,9'-spirobifluorene, whose synthesis is described, for example, by R. G. Clarkson, M. Gomberg, J.Am.Chem.Soc. 52 (1930) 2881.

Compounds of the formula (I) in which $K^a$=L=M=$N^a$, and $O^a$=$P^a$=H, can be prepared, for example, starting from a tetrahalogenation in positions 2,2',7,7' of 9,9'-spirobifluorene following by a substitution reaction (see, for example, U.S. Pat. No. 5,026,894) or via tetraacetylation in positions 2,2',7,7' of 9,9'-spirobifluorene followed by C-C-blinking after conversion of the acetyl groups into aldehyde groups or build-up of heterocyclic rings after conversion of the acetyl groups into carboxyl groups.

Compounds of the formula (I) in which $K^a=M=P^a=O^a=H$ and $N^a=L$ can be prepared analogously to those of the formula IIIa, with the stoichiometric ratios in the reaction being selected in such a way that positions 2,2' or 7,7' are functionalized (see, for example, J. H. Weisburger, E. K. Weisburger, F. E. Ray, J. Am. Chem. Soc. 72 (1959) 4253; F. K. Sutcliffe, H. M. Shahidi, D. Paterson, J. Soc. Dyers Colour 94 (1978) 306, and G. Haas, V. Prelog, Helv. Chim. Acta 52 (1969) 1202).

Compounds of the formula (IIIc) can be prepared, for example, by dibromination in the 2,2'-position followed by diacetylation in the 7,7'-position of 9,9'-spirobifluorene followed by reaction analogously to the compounds IIIa.

Compounds of the formulae (IIIe)–(IIIg) can be prepared, for example, through selection of suitably substituted starting compounds in the synthesis of the spirobifluorene, for example 2,7-dibromospirobifluorene can be synthesized from 2,7-dibromofluorenone and 2,7-dicarbethoxy-9,9-spirobifluorene can be synthesized using 2,7-dicarbethoxyfluorenone. The free 2',7'-positions of the spirobifluorene can then be further substituted independently.

For the synthesis of the groups $K^a$, L, M and $N^a$, reference is made, for example, to DE-A 23 44 732, 24 50 088, 24 29 093, 25 02 904, 26 36 684, 27 01 591 and 27 52 975 for compounds containing 1,4-phenylene groups; DE-A 26 41 724 for compounds containing pyrimidine-2,5-diyl groups; DE-A 40 26 223 and EP-A 0 391 203 for compounds containing pyridine-2,5-diyl groups; DE-A 32 31 462 for compounds containing pyridazine-3,6-diyl groups; N. Miyaura, T. Yanagi and A. Suzuki in Synthetic Communications 11 (1981) 513 to 519, DE-A-3 930 663, M. J. Sharp, W. Cheng, V. Snieckus in Tetrahedron Letters 28 (1987), 5093; G. W. Gray in J. Chem. Soc. Perkin Trans II (1989) 2041 and Mol. Cryst. Liq. Cryst. 172 (1989) 165, Mol. Cryst. Liq. Cryst. 204 (1991) 43 and 91; EP-A 0 449 015; WO 89/12039; WO 89/03821; EP-A 0 354 434 for the direct linking of aromatic compounds and heteroaromatic compounds;

The preparation of disubstituted pyridines, disubstituted pyrazines, disubstituted pyrimidines and disubstituted pyridazines is described, for example, in the corresponding volumes of the series "The Chemistry of Heterocyclic Compounds" by A. Weissberger and E. C. Taylor (editors).

For further variants, we also refer to the working examples.

The compounds according to the invention are suitable as laser dyes.

A laser is a light-amplifying device which is capable of generating high-intensity, coherent, monochromatic light radiation which is concentrated in a well parallelized beam, which is generally known as a laser beam. A typical laser comprises an optical resonator containing a laser-active material, i.e. a laser medium, which can be a solid, a liquid or a gas. On operation of the laser, the atoms or molecules of the laser medium are excited until they emit laser radiation, i.e. until they emit photons or light quanta. In order to excite the atoms or molecules into the laser radiation-emitting state, i.e. to pumping, they are subjected to bombardment with electrons or photons. On emission of photons, these photons can initiate premature emission of similar photons by other molecules, and together these form the laser beam. Lasers have a variety of applications in a wide variety of areas, such as drilling, spectroscopy, welding, cutting, information transmission, analytical methods, surgery and photochemistry.

A laser can usually only work in a small region of the visible spectrum since it depends on the laser medium used, especially as the wavelengths emitted in a specific energy transition in a given laser medium can only be adjusted over a very small region of the visible spectrum. It is therefore necessary to have available a wide variety of different laser media in order to privide lasers with the capability to work over the entire visible spectral region.

The present invention is suitable for the operation of a dye laser which comprises a pump light source which has the capability of exciting a dye to emit laser radiation.

The present invention is furthermore suitable for the emission of laser radiation at various wavelengths by exposing a laser medium to a suitable pump light source which contains an organic laser dye in accordance with this invention in order to excite the laser medium to emit radiation.

Details on the use of the application according to the invention are also given in the European patent application with the title "Organic Solid State Light Sources With Narrow Band Width Emission" of Feb. 4, 1998 (applicant Hoechst Research and Technology GmbH & Co. KG), which is expressly incorporated herein by way of reference.

Furthermore, the compounds according to the invention can be used, for example, as:
a) electroluminescent materials (see, for example, EP-A 0 676 461)
b) charge-transport layer in photovoltaic cells (see, for example, WO-A 97/106 17) or radiation detectors (see, for example, DE-A 196 46 411 or PCT/EP97/0605).
c) as materials in nonlinear optics (see, for example, EP-A 0 768 563)
d) as optical brighteners (see, for example, DE-A 196 45 063).

The cited specifications are expressly incorporated herein by way of reference.

The invention is explained in greater detail by means of the examples, without being restricted thereby.

EXAMPLES

A Syntheses

A 1 Precursors:

A 1.1 Synthesis of 9,9'-spirobifluorene-2-boronic Acid:

(a) 2-Bromo-9-(biphenyl-2-yl)fluoren-9-ol 2.34 g of magnesium turnings and a few crystals of iodine were introduced into a 500 ml four-necked flask fitted with reflux condenser and dropping funnel which had been dried by heating with a hairdryer and blanketed with $N_2$. After about 20 ml of dry THF had been added, about 5 ml of 22.5 g of 2-bromobiphenyl were firstly added dropwise as rapidly as possible and the mixture was heated at the drop addition point. After the reaction had commenced, the remainder of the 2-bromobiphenyl was added at such a rate that the reaction mixture boiled of its own accord. About 180 ml of THF were subsequently added, and the mixture was then refluxed for 2 hours.

The hot, clear Grignard solution was decanted from unreacted Mg into a 1000 ml four-necked flask. The mixture was cooled to 0° C., and a solution of 25.0 g of 2-bromofluoren-9-one in 290 ml of THF was added dropwise over the course of 20 minutes. After the ice bath had been removed, the yellow suspension was stirred at room temperature for one hour and then refluxed for 2 hours. After cooling, the white solid which precipitated was filtered off with suction, washed and hydrolyzed in a mixture of 180 ml of ice-water and about 5 ml of conc. HCl. The mixture was extracted with about 300 ml of $CHCl_3$. After the organic phases had been combined, they were extracted twice with aqueous $NaHCO_3$ solution and subsequently with water. After the mixture had been dried and the solvent stripped off, the product was further purified by reprecipitation from methylene chloride/hexane. The product was obtained as a white, crystalline powder.

Yield: 28.8 g (72%).

Melting point: 169–170° C.

1H-NMR (400 MHz, d-DMSO): δ=8.41–8.39 (pdd; 1H), 7.56–7.51 (ptd, 1H), 7.38–7.26 (m, 3H), 7.22–7.17 (m, 3H), 7.14–7.13 (pd, 1H), 7.09–7.06 (m, 1H), 6.86–6.82 (m, 1H), 6.78–6.76 (pdd, 1H), 6.65–6.57 (pd, 2H), 6.23 (s, 1H), 5.95, 5.79 (2×s, 2H).

(b) 2-Bromo-9,9'-spirobifluorene 47.0 g of 2-bromo-9-(biphenyl-2-yl)fluoren-9-ol were refluxed for 2.5 hours in 114 ml of 99.8% acetic acid with addition of 1.5 ml of conc. HCl.

The precipitate was filtered off with suction and washed with water. After drying, the product was obtained as a white, crystalline powder.

Yield: 44.4 g (99%).

Melting point: 183° C.

1H-NMR (400 MHz, $CDCl_3$): δ=7.84 (dd, 2H), 7.81 (dd, 1H), 7.70 (d, 1H), 7.49 (dd, 1H), 7.37 (m, 3H), 7.12 (m, 3H), 6.85 (d, 1H), 6.72 (m, 3H).

(c) Synthesis of 9,9'-spirobifluorene-2-boronic Acid 1.84 g of magnesium turnings and a few crystals of iodine were introduced into a 2000 ml four-necked flask fitted with reflux condenser and dropping funnel which had been dried by heating and blanketed with $N_2$. About 25 ml of a solution of 30.0 g of 2-bromo-9,9'-spirobifluorene in 120 ml of dry THF were firstly added dropwise as quickly as possible, and the mixture was heated at the drop addition point. After the reaction had commenced, the remainder of the starting-material solution was added at such a rate that the reaction mixture boiled of its own accord. About 1100 ml of THF were subsequently added, and the mixture was then refluxed for 2 hours. The clear Grignard solution was cooled to room temperature and added dropwise to a mixture of 8.68 g of freshly distilled trimethyl borate in about 100 ml of THF under $N_2$ in a 2000 ml four-necked flask over the course of four hours at such a rate that the internal temperature was between −70 and −75° C. The batch was then slowly warmed to room temperature. 100 g of ice-water/3 ml of 95–97% $H_2SO_4$ were added to the white suspension. The undissolved, inorganic precipitate was filtered off with suction and rinsed, and the mother liquor was extracted twice with aqueous NaCl solution. The organic phase was dried over $MgSO_4$, and the solvent was stripped off. The crude product obtained was purified by stirring twice with hexane and twice with acetonitrile at elevated temperature. After drying, the product was obtained as a white powder.

Yield: 21 g (77%).

1H-NMR (400 MHz, d-DMSO): δ=8.03–8.01 (pdd, 2H), 7.99–7.97 (pdd, 1H), 7.89 (s, 1H), 7.88–7.86 (pdd, 1H), 7.42–7.38 (m, 3H), 7.16–7.11 (m, 3H), 7.08 (ps, 1H), 6.60–6.59 (m, 3H).

A 1.2 Synthesis of 2,2',7,7'-tetrabromospiro-9,9'-bifluorene:

This compound was prepared analogously to the procedure in EP-A 676 461.

A 1.3 Synthesis of 2-bromo-2',7,7'-triiodo-9,9'-spirobifluorene

A suspension of 14.6 g of bis(trifluoroacetoxy)iodobenzene in 70 ml of $CHCl_3$ was added dropwise over the course of 1.2 hours under $N_2$ to a vigorously stirred solution of 6.20 g of 2-bromo-9,9'-spirobifluorene and 8.03 g of iodine in 35 ml of $CHCl_3$ in a 250 ml four-necked flask fitted with rising pipe and dropping funnel, the internal temperature during the addition being 0–5° C. The mixture was stirred at 5–10° C. for a further one hour and then at room temperature overnight. The precipitate was filtered off with suction. About 500 ml of $CHCl_3$ were added thereto, and the suspension was stirred in an aqueous $Na_2SO_3$ solution which had been rendered alkaline using $NaHCO_3$. The organic phase was separated off and washed by shaking with water and evaporated to dryness.

The red mother liquor was washed by shaking successively with an aqueous solution of $Na_2SO_3$ and $NaHCO_3$, dried over $Na_2SO_4$ and evaporated to dryness.

According to TLC, the two fractions were identical. About 200 ml of acetone were added thereto, and the mixture was stirred vigorously for one hour.

Filtration with suction and drying gave the product 2-bromo-2',7,7'-triiodo-9,9'-spirobifluorene as a white powder.

Yield: 9.1 g (75%).

$^1$H-NMR (400 MHz, $CDCl_3$): δ=7.75–7.72 (pdt, 3H), 7.68–7.66 (pd, 1H), 7.57–7.52 (m, 4H), 7.00 (pt, 3H), 6.81–6.80 (pd, 1H).

A 1.4 Synthesis of 2',7,7'-tri-(9,9'-spirobifluoren-2-yl)-9,9'-spirobifluorene-2-boronic Acid (a) Synthesis of 2-bromo-2',7,7'-tri(9,9'-spirobifluoren-2-yl)-9,9'-spirobifluorene:

5.00 g of 2-bromo-2',7,7'-triiodo-9,9'-spirobifluorene, 7.70 g of 9,9'-spirobifluorene-2-boronic acid and 5.89 g of $K_2CO_3$, as well as 25 ml of toluene, 30 ml of water and 60 ml of THF were introduced into a 250 ml three-necked flask fitted with reflux condenser, and the mixture was stirred for 45 minutes at about 60° C. under $N_2$ in order to remove oxygen. 370 mg of $Pd(PPh_3)_4$ were subsequently added, and the mixture was refluxed for 48 hours.

After the reaction mixture had been filtered through a fluted filter, 100 mg of KCN were added to the yellow filtrate, and the mixture was heated, with addition of a few drops of conc. aqueous $NaHCO_3$ solution, for one hour at about 70° C. The phases were separated, and the aqueous phase was extracted with 50 ml of $CH_2Cl_2$. The combined organic phases were dried over $Na_2SO_4$, evaporated to dryness and dried.

The crude product was passed through a silica gel column using hexane/$CH_2Cl_2$=2:1 as eluent. Filtration with suction and drying give the product as a white powder.

Yield: 5.05 g (58%)

$^1$H-NMR (400 MHz, $CDCl_3$): δ=7.83–7.80 (pd, 6H), 7.77–7.75 (m, 3H), 7.71–7.65 (m, 6H), 7.63–7.61 (pd, 1H), 7.43–7.41 (dd, 1H), 7.36–7.29 (m, 15H), 7.08–7.03 (m, 9H), 6.85–6.82 (m, 4H), 6.77–6.76 (pd, 2H), 6.73–6.72 (pd, 1H), 6.71–6.67 (m, 6H), 6.65–6.63 (pd, 3H).

(b) Synthesis of 2',7,7'-tri(9,9'-spirobifluoren-2-yl)-9,9'-spirobifluorenyl-2-boronic acid 2.8 ml of a 1.6 M solution of n-BuLi in hexane were slowly added dropwise over the course of 30 minutes to a clear solution of 2.00 g of 2-bromo-2',7,7'-tri(9,9'-spirobifluoren-2-yl)-9,9'-spirobifluorene in 40 ml of abs. THF at −74° C. under $N_2$ in a 100 ml three-hecked flask fitted with internal thermometer and septum, during which the reaction mixture became a yellow color. The mixture was allowed to warm to −10° C. (green coloration of the solution) and re-cooled to −74° C., and 620 mg of trimethyl borate were added to the clear solution, which remained green, over the course of 10 minutes. The batch was then stirred at room temperature over the weekend (yellow coloration of the solution).

After 60 ml of water had been added to the yellow reaction mixture, the mixture was extracted three times with 30 ml of $CHCl_3$ each time, and the combined organic phases were extracted with 30 ml of water. The organic phase was dried over $Na_2SO_4$, the solvent was stripped off, and the product was passed through a silica gel column using $CH_2Cl_2$/hexane=1:1 as eluent, becoming increasingly polar (2:1, 3:1, pure $CH_2Cl_2$, $CH_2Cl_2$/MeOH, pure MeOH). The product was subsequently extracted by stirring in a mixture of 50 ml of acetonitrile and 25 ml of water at about 50° C. for 30 minutes. Filtration with suction and drying gave the product as a white powder.

Yield: 1.03 g (55%).

Since the boronic acid was a mixture of boronic acid and various anhydrides, interpretation of the NMR spectrum was not possible. A small sample was analyzed by mass spectroscopy after esterification using ethylene glycol:

MS (FD, 8 kV): m/e (%)=1259.9 (100)[$M^+$-B(OCH$_2$)$_2$].

A 1.5 Synthesis of 2,2',7,7'-tetrakis(4-iodophenyl)-9,9'-spirobifluorene 4.94 g of iodine and 9.67 g of bis(trifluoroacetoxy)iodobenzene were added at room temperature to a solution of 6.00 g of 2,2',7,7'-tetraphenyl-9,9'-spirobifluorene (prepared as described in EP-A 676 461) in 100 ml of $CHCl_3$ in a 250 ml two-necked flask fitted with reflux condenser and drying tube.

After the mixture had been stirred for 30 minutes, the precipitated solid was filtered off with suction, washed with $CHCl_3$, dried and recrystallized three times from toluene. The product 2,2',7,7'-tetra(4-iodophenyl)-9,9'-spirobifluorene was obtained as a white powder.

Yield: 2.8 g (26%).

$^1$H-NMR (400 MHz, CDCl$_3$): δ=7.95–7.93 (pd, 1H), 7.63–7.59 (m, 3H), 7.18–7.15 (m, 2H), 6.94–6.93 (pd, 1H).

A 2 Compounds According to the Invention

A 2.1 Synthesis of 2,2',7,7'-tetrakis(9,9'-spirobifluoren-2-yl)-9,9'-spirobifluorene 967 mg of 2,2',7,7'-tetrabromo-9,9'-spirobifluorene, 2.42 g of 9,9'-spirobifluorene-2-boronic acid and 1.86 g of $K_2CO_3$, as well as 10 ml of toluene, 15 ml of water and 25 ml of abs. THF were introduced into a 100 ml three-necked flask fitted with reflux condenser and internal thermometer and stirred for 45 minutes at about 60° C. under $N_2$ in order to remove oxygen. The catalyst was then added, and the mixture was refluxed at an internal temperature of 75° C. for a total of 46.5 hours. The mixture was cooled to room temperature and filtered with suction, the precipitate was dissolved in about 30 ml of $CHCl_3$, 10 ml of conc. aqueous $NaHCO_3$ solution were added to the solution, and a solution of about 400 mg of KCN in 50 ml of water-was added. The mixture was subsequently refluxed for one hour. The organic phase was separated off and dried, and the solvent was stripped off. The crude product was recrystallized twice from dioxane. The product was obtained as a white powder.

Yield: 1.60 g (67%)

Melting point (DSC): 449° C. ($T_g$=273° C.).

$^1$H-NMR (400 MHz, CDCl$_3$): δ=7,82–7.80 (pd, 2H), 7.75–7.73 (pd, 1H), 7.66–7.64 (pq, 2H), 7.35–7.26 (m, 5H), 7.07–7.02 (m, 3H), 6.83 (pd, 1H), 6.78–6.77 (pd, 1H), 6.68–6.66 (pd, 2H), 6.64–6.62 (pd, 1H).

A 2.2 Synthesis of 2,2',7,7'-tetra[4-(9,9'-spirobifluoren-2-yl)phenyl]-9,9'-spirobifluorene 1.40 g 2,2',7,7'-tetrakis(4-iodophenyl)-9,9'-spirobifluorene, 1.98 g of 9,9'-spirobifluorene-2-boronic acid and 1.52 g of $K_2CO_3$, as well as 20 ml of toluene, 15 ml of water and 25 ml of THF were introduced into a 100 ml three-necked flask fitted with reflux condenser and internal thermometer and stirred for 45 minutes at about 60° C. under $N_2$ in order to remove oxygen. 70 mg of Pd(PPh$_3$)$_4$ were subsequently added, and the mixture was refluxed for 48 hours. The course of the reaction was monitored by TLC.

The reaction mixture was concentrated somewhat, and the precipitated solid was filtered off with suction, washed with water and refluxed for 2.5 hours in a mixture of 30 ml of $CHCl_3$ and 700 mg of KCN in 30 ml of $H_2O$ with addition of a few drops of conc. aqueous $NaHCO_3$ solution. The mixture was subsequently refluxed for 45 minutes in 50 ml of hexane, filtered off with suction, rinsed and dried. The product was finally recrystallized twice from dioxane. The product was obtained as a white powder.

Yield: 1.28 g (55%)

Melting point (DSC): 448° C. ($T_g$=272° C.).

$^1$H-NMR (400 MHz, CDCl$_3$): δ=7.85–7.81 (m, 5H), 7.55–7.51 (m, 2H), 7.36–7.29 (m, 7H), 7.10–7.05 (m, 3H), 6.91 (pd, 1H), 6.85 (pd, 1H), 6.74–6.69 (m, 3H).

A 2.3 Synthesis of 2,2',7,7'-tetrakis[(2',7,7'-tri-(9,9'-spirobifluoren-2-yl)-9,9'-spirobifluoren-2-yl]-9,9'-spirobifluorene 75.0 mg of 2,2',7,7'-tetrabromo-9,9'-spirobifluorene, 690 mg of 2',7,7'-tri(9,9'-spirobifluoren-2-yl)-9,9'-spirobifluorenespirobifluorene-2-boronic acid and 145 mg of $K_2CO_3$, as well as 4 ml of toluene, 6 ml of water and 10 ml of THF were introduced into a 100 ml two-necked flask fitted with reflux condenser and stirred for 45 minutes at room temperature under $N_2$ in order to remove oxygen. 2.1 mg of Pd(PPh$_3$)$_4$ were subsequently added, and the mixture was refluxed at an internal temperature of 75° C. for a total of 140 hours.

A solution of 60 mg of KCN in 30 ml of $H_2O$ was added to the two-phase reaction mixture, and the mixture was heated at about 50° C. for 1 hour. The organic phase was separated off and precipitated using 100 ml of MeOH, and the precipitated solid was filtered off with suction, dried and passed through a silica gel column using hexane/$CH_2Cl_2$=1:1 as eluent. The product was obtained as a white powder after double recrystallization from dioxane.

Yield: 200 mg (31%).

Since the complex H-NMR did not allow a precise structure determination, the compound was analyzed by high-resolution mass.

MS (MALDI-TOF): m/e=5346.63 [$M^+$]. Theoretical value: 5346.65

B Use of the Compounds According to the Invention in Emission Devices

Thin (100 nm) amorphous films were produced from the compounds A 2.1 to A 2.3 by spin coating of solutions of the respective compounds in chlorobenzene. To this end, the compounds were firstly completely dissolved (10 mg/ml; the solutions were prepared by stirring the compounds for about 15 hours at 50° C. under $N_2$) and subsequently spin-coated at suitable rotational speeds.

Bright blue photoluminescence with extremely high efficiency was obtained for all three compounds. To our knowledge, these compounds have the highest PL efficiencies ever reported in the solid, undiluted state:

| Compound | $\lambda_{PL\ film}$ [nm] | $\Phi_{PL\ film}$ [%] |
|---|---|---|
| A 2.1 | 403, 425 | >90 |
| A 2.2 | 414, 435 | >90 |
| A 2.3 | 425, 447 | >90 |

Furthermore, experiments were carried out with the compounds with respect to their properties as laser dyes (amplified spontaneous emission=ASE).

To this end, the films produced were optically pumped (pulsed nitrogen laser; excitation at 337 nm) and the line narrowing was followed as a function of the excitation intensity. The following results were obtained here. These results were compared with those from two compounds not according to the invention.

| Compound | Beginning of significant line narrowing [µJ/cm²] | Line width of the emission at half maximum height [nm][3] |
|---|---|---|
| A 2.1 | 2 | 3.5 |
| A 2.2 | 2 | 3.1 |
| A 2.3 | 1.3 | 2.3 |
| Spiro-6-PP[1] | 4 | 8 |
| Spiro-4-PP[2] | 30 | 46 |

[1] 2,2',7,7'-tetrakis(4-biphenyl)-9,9'-spirobifluorene
[2] 2,2',7,7'-tetraphenyl-9,9'-spirobifluorene
[3] Excitation intensity: 10 µJ/cm²

These measurements confirm that the compounds according to the invention exhibit the phenomenon of ASE even at extremely low excitation energies. This predestines the compounds according to the invention for use in optically pumped lasers. Electrically pumped organic lasers are currently not available; should these be developed, however, the compounds according to the invention are extremely suitable therefor owing to their extremely high PL efficiency in the solid—undiluted—state and their high thermal stability.

What is claimed is:

1. A compound of the formula (I):

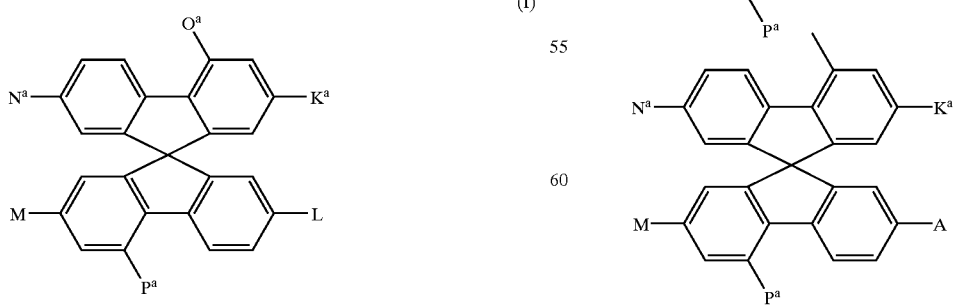

where $K^a$, $L$, $M$, $N^a$, $O^a$ and $P^a$, independently of one another, are identical or different and are

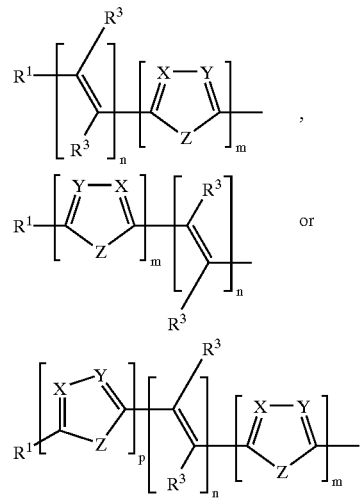

where the symbols and indices have the following meaning:
$R^3$: H, $C_1$–$C_{22}$-alkyl, $C_6$–$C_{14}$-aryl, $C_5$–$C_{20}$-alkylaryl or $C_5$–$C_{20}$-arylalkyl;
m: 1, 2, 3, 4, 5 or 6;
n and p: independently of one another, identically or differently, 0, 1, 2, 3, 4, 5 or 6;
X and Y: CR;
Z: $CR_2$, —CH═CH—, or —$CR^2$═$CR^2$—;
R: H, $C_1$–$C_{22}$-alkyl (linear, branched or cyclic), or $C_6$–$C_{14}$-aryl,
$R^1$: independently of one another, identically or differently, R, A, B, or C,
where

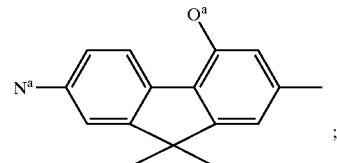

A

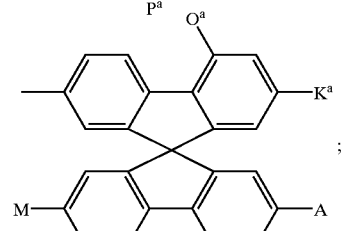

B

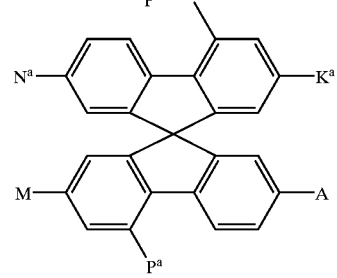

C where at least one radical $R^1$ is A, B or C and the number of groups of A, B or C is from 1 to 50 with the total number of groups of A, B and C being up to 50;

R$^2$ is, identically or differently, H or a hydrocarbon radical having 1 to 30 carbon atoms, with the proviso that the following compounds are excluded from formula (I)

when (a) O$^a$, K$^a$, M and L simultaneously, R$^1$ as R, then K$^a$ and N$^a$ cannot have R$^1$ as A or B, and (b) O$^a$, K$^a$, M and p simultaneously have R$^1$ as R, then N$^a$ and L cannot have R$^1$ as A or B.

2. The compound as claimed in claim 1, wherein R$^1$ for K$^a$, L, M and N$^a$ in the formula (I) is, independently of one another, identically or differently, A, B or C.

3. The compound as claimed in claim 1, wherein O$_a$ and P$_a$ in the formula (I) are H.

4. The compound as claimed in claim 1, wherein R$^1$ in the formula (I) is, identically or differently, A, B or C.

5. The compound as claimed in claim 1, wherein R$^1$ is R or A, where at least one R$^1$ is A.

6. The compound as claimed in claim 1, wherein R$^1$ is A.

7. The compound as claimed in claim 1, wherein the number of groups of A, B or C is from 1 to 20 with the total number of groups of A, B and C being up to 20.

8. The compound as claimed in claim 1, wherein the number of groups of A, B or C is from 1 to 10 with the total number of groups of A, B and C being up to 10.

9. A compound of the formula (II):

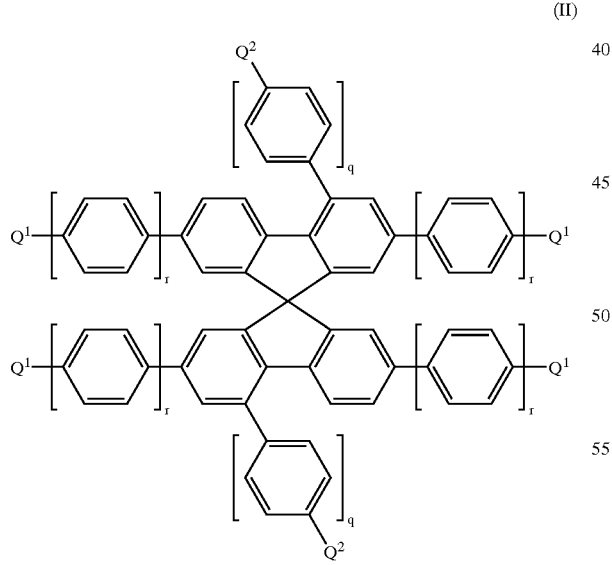

(II)

where the symbols and indices have the following meanings:

q and r: independently of one another, identically or differently, 0, 1, 2, 3, 4, 5 or 6;

Q$^1$ is of the formula (III):

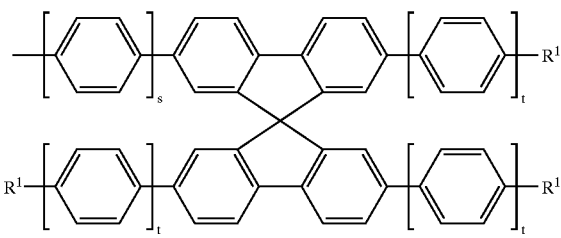

(III)

Q$^2$ independently of one another, identically or differently, H or is of the formula (III) as defined above wherein s and t: independently of one another, identically or differently, is 0, 1, 2, 3 or 4;

R$^1$: independently of one another, identically or differently, is R or A, B or C, where

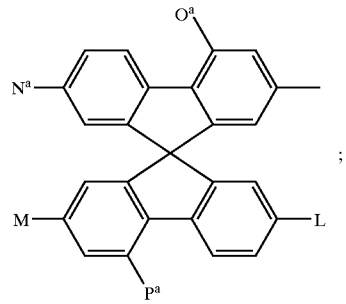

A

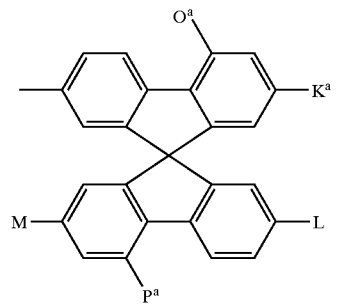

B

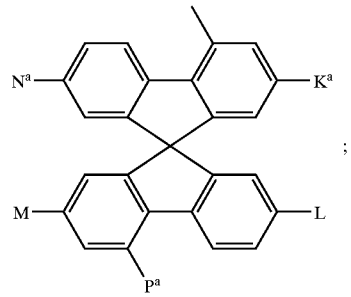

C where at least one radical R$^1$ is A, B, or C and the number of groups of A, B or C is from 1 to 50 with the total number of groups of A, B and C being up to 50;

where $K^a$, L, M, $N^a$, $O^a$ and $P^a$, independently of each other, are identical or different and are

A

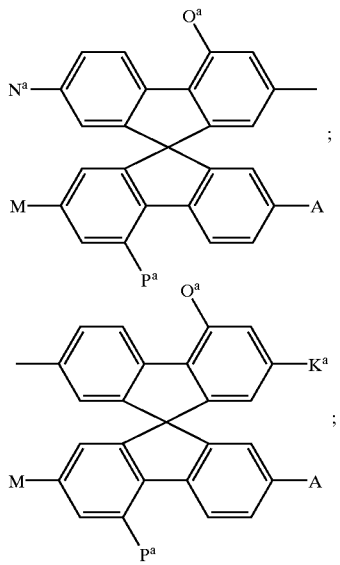

R²: identically or differently, H or a hydrocarbon radical having 1 to 30 carbon atoms;

R³: H, $C_1$–$C_{22}$-alkyl, $C_6$–$C_{14}$-aryl, $C_5$–$C_{20}$-alkylaryl or $C_5$–$C_{20}$-arylalkyl;

m, n, and p: independently of one another, identically or differently, 0, 1, 2, 3, 4, 5 or 6;

X and Y: CR;

Z: $CR_2$, —CH=CH—, or —CR²=CR²—;

R: H, $C_1$–$C_{22}$-alkyl (linear, branched or cyclic), or $C_6$–$C_{14}$-aryl.

10. The compound of claim 9, wherein the symbols and indices have the following meanings:

$Q^1$: is of the formula (IIIa):

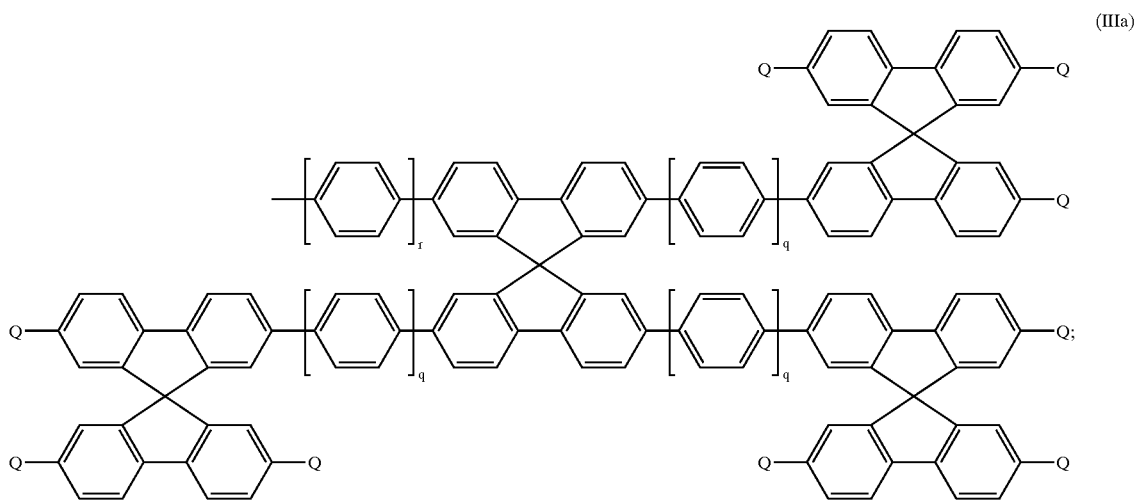

(IIIa)

$Q^2$: is of the formula (IIIa) or H;

where s and t: independently of one another, identically or differently, are 0, 1, 2, 3, or 4; and Q: independently of one another, identically or differently, is R or $Q^1$.

11. The compound as claimed in claim 9, wherein the number of groups of A, B or C is from 1 to 20 with the total number of groups of A, B and C being up to 20.

12. The compound as claimed in claim 9, wherein the number of groups of A, B or C is from 1 to 10 with the total number of groups of A, B and C being up to 10.

-continued

C

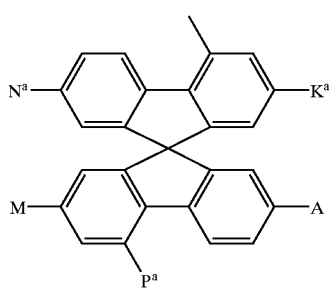

* * * * *

UNITED STATES PATENT AND TRADEMARK OFFICE
CERTIFICATE OF CORRECTION

PATENT NO. : 6,861,567 B2  Page 1 of 3
APPLICATION NO. : 10/243302
DATED : March 1, 2005
INVENTOR(S) : Hubert Spreitzer et al.

It is certified that error appears in the above-identified patent and that said Letters Patent is hereby corrected as shown below:

In the Specification:

At Col. 1 lines 30-40, the formula
"
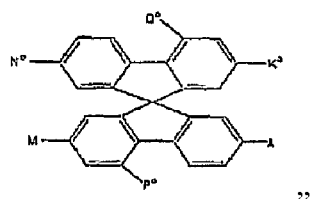
"

should read
--
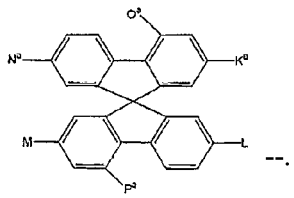
--.

On Col. 2, lines 15-50,

"A                B                C
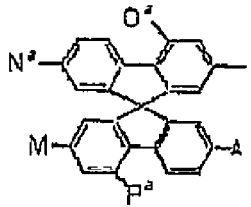 ; 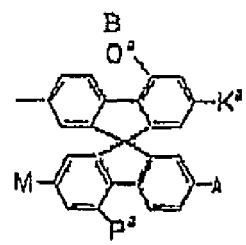 ; 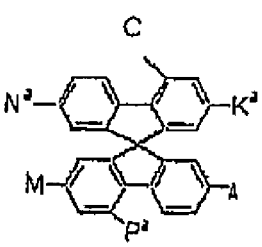
"

should read
--
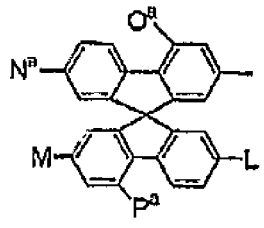 ; 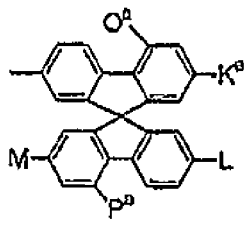 ; 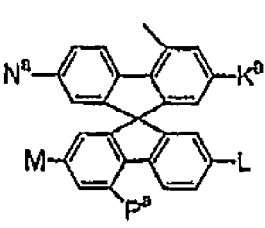
A                B                C
--.

UNITED STATES PATENT AND TRADEMARK OFFICE
CERTIFICATE OF CORRECTION

PATENT NO.        : 6,861,567 B2
APPLICATION NO.   : 10/243302
DATED             : March 1, 2005
INVENTOR(S)       : Hubert Spreitzer et al.

It is certified that error appears in the above-identified patent and that said Letters Patent is hereby corrected as shown below:

In the Claims:

In Claim 1, Col. 2 lines 34-65,

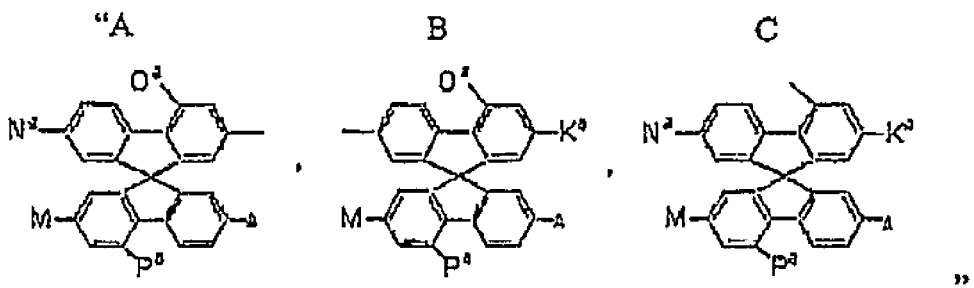

should read

--

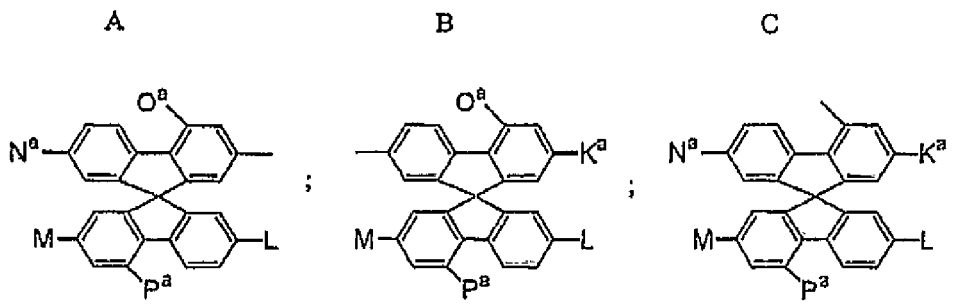

--

In Claim 3, Col. 13, line 21 "$O_a$" should read --$O^a$--.

In Claim 3, Col. 13, line 22 "$P_a$" should read --$P^a$--.

In Claim 9, Col. 13, line 67 "0,1" should read --0, 1--.

UNITED STATES PATENT AND TRADEMARK OFFICE
CERTIFICATE OF CORRECTION

PATENT NO.       : 6,861,567 B2
APPLICATION NO.  : 10/243302
DATED            : March 1, 2005
INVENTOR(S)      : Hubert Spreitzer et al.

It is certified that error appears in the above-identified patent and that said Letters Patent is hereby corrected as shown below:

In Claim 9, Col. 15, lines 3-65

"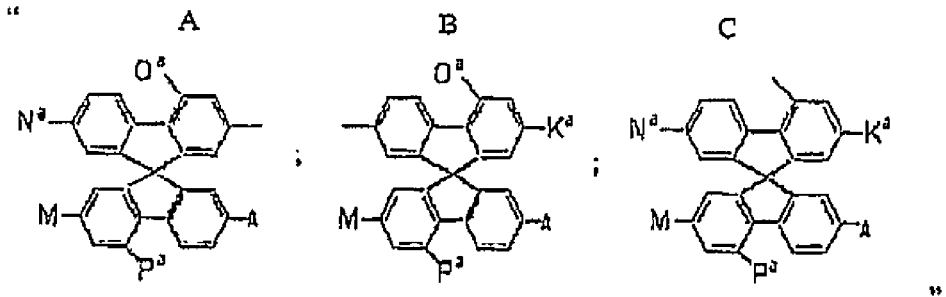"

should read

--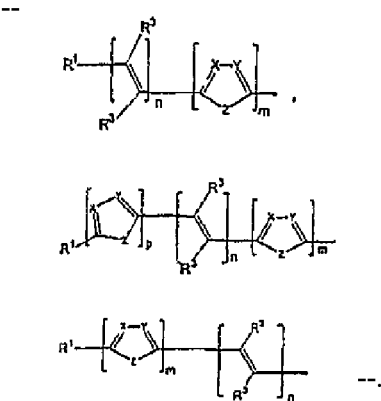--.

Signed and Sealed this

First Day of January, 2008

JON W. DUDAS
*Director of the United States Patent and Trademark Office*